(12) United States Patent
Iwata et al.

(10) Patent No.: US 8,167,824 B2
(45) Date of Patent: May 1, 2012

(54) SENSATION DETECTION PRESENTATION APPARATUS AND WALKING REHABILITATION SUPPORTING APPARATUS

(75) Inventors: Hiroyasu Iwata, Tokyo (JP); Shigeki Sugano, Tokyo (JP)

(73) Assignee: Waseda University, Tokyo (JP)

( * ) Notice: Subject to any disclaimer, the term of this patent is extended or adjusted under 35 U.S.C. 154(b) by 354 days.

(21) Appl. No.: 12/514,381

(22) PCT Filed: May 5, 2007

(86) PCT No.: PCT/JP2007/059401
§ 371 (c)(1),
(2), (4) Date: May 11, 2009

(87) PCT Pub. No.: WO2008/062572
PCT Pub. Date: May 29, 2008

(65) Prior Publication Data
US 2010/0041959 A1    Feb. 18, 2010

(30) Foreign Application Priority Data

Nov. 22, 2006    (JP) .................................. 2006-315781

(51) Int. Cl.
*A61B 5/103* (2006.01)
*A61B 5/117* (2006.01)
(52) U.S. Cl. ........................................................ 600/592
(58) Field of Classification Search ................... 600/592
See application file for complete search history.

(56) References Cited

U.S. PATENT DOCUMENTS 4,760,850 A * 8/1988 Phillips et al. ............. 340/407.1
2007/0073196 A1   3/2007 Tanaka et al.

FOREIGN PATENT DOCUMENTS

| EP | 1625841 A1 | 2/2006 |
|---|---|---|
| JP | 07-204235 A | 8/1995 |
| JP | 2004-141275 A | 5/2004 |
| JP | 2007-061260 A | 3/2007 |
| WO | 2004/103244 A1 | 12/2004 |

OTHER PUBLICATIONS

International Search Report of PCT/JP2007/059401, Mailing Date of Aug. 7, 2007.

* cited by examiner

*Primary Examiner* — Max Hindenburg
*Assistant Examiner* — Emily Lloyd
(74) *Attorney, Agent, or Firm* — Westerman, Hattori, Daniels & Adrian, LLP

(57) ABSTRACT

It is intended to feed back any somatic sensation information on given body surface portion in easily understandable form without the use of special sensations, such as visual and auditory sensations. Walking rehabilitation supporting apparatus (10) comprises sensation detection unit (11) for detecting the sole pressure of patient (H); sensation presentation unit (13) for imparting given stimuli to the patient (H); and control unit (15) for controlling the behavior of the sensation presentation unit (13) so as to impart stimuli corresponding to the sole pressure detected by the sensation detection unit (11). The sensation detection unit (11) is disposed so as to be capable of detecting the sole pressure on a paralyzed side, and the sensation presentation unit (13) is fitted to a body surface portion of sensation superior to that of the sole.

3 Claims, 5 Drawing Sheets

(A)

(B)

SENSATION DETECTION PRESENTATION APPARATUS AND WALKING REHABILITATION SUPPORTING APPARATUS

TECHNICAL FIELD

The present invention relates to a sensation detection presentation apparatus and a walking rehabilitation supporting apparatus, and more particularly to a sensation detection presentation apparatus and a walking rehabilitation supporting apparatus that can feed back somatic sensation information on a given body surface portion to the body surface portion or a different body surface portion using somatic sensation.

BACKGROUND ART

Stroke patients with disorders such as motor paralysis may acquire wrong walking behavior without proper training at early stages. For example, hemiplegic patients due to stroke undergo walking rehabilitation to acquire walking behavior of properly placing a foot sole on a paralyzed side on the ground. At this time, the foot sole on the paralyzed side has less sensation, and thus sensation on the paralyzed side is fed back using different sensation so that a patient can perceive to acquire proper movement on the basis of the perception, which is a therapy referred to as biofeedback. The sensations include somatic sensations including cutaneous sensations such as tactile, pressure, warm, cold, and pain sensations, and special sensations such as visual, auditory, gustatory, and olfactory sensations.

As apparatuses for such a biofeedback therapy, a visual sensation biofeedback apparatus (see Patent Document 1) and an auditory sensation biofeedback apparatus (see Patent Document 2) are disclosed. The visual sensations biofeedback apparatus displays distribution changes in sole pressure on a display device (monitor), and allows a patient to recognize a proper state using visual sensation of the patient. Also, the auditory sensation biofeedback apparatus converts distribution changes in sole pressure into sound, and allows a patient to recognize a proper state using auditory sensation of the patient.

Patent Document 1: Japanese Patent Laid-Open No. 7-204235

Patent Document 2: Japanese Patent Laid-Open No. 2004-141275

DISCLOSURE OF THE INVENTION

Problems to be Solved by the Invention

However, for the visual sensation biofeedback apparatus in Patent Document 1, for example, when a hemiplegic patient undergoes walking training, the patient must watch the monitor, and walking training in a wide range is impossible in view of safety and a system configuration. Further, for the auditory sensation biofeedback apparatus in Patent Document 2, changes in sole pressure with time within a foot sole region are indicated by intensities of sound or melodies, which requires information conversion with a high load, and thus it is difficult for the patient to accurately understand the state.

The present invention is achieved in view of such disadvantages, and has an object to provide a sensation detection presentation apparatus and a walking rehabilitation supporting apparatus that can feed back somatic sensation information on a given body surface portion in easily understandable form without the use of special sensations such as visual and auditory sensations.

Means for Solving the Problems (1) To achieve the object, the present invention includes: sensation detection means for detecting somatic sensation information on a first body surface portion of a user; and sensation presentation means for presenting somatic sensation information corresponding to the somatic sensation information detected by the sensation detection means to the first body surface portion or a second body surface portion different from the first body surface portion of the user.

(2) It is preferable that the sensation presentation means includes a stimulus imparting device for mechanically imparting stimulus to skin so that the user receives touch-pressure sensation, vibratory sensation and/or movement sensation, and the stimulus imparting device imparts stimulus to the skin at intensity corresponding to the level of the somatic sensation detected by the sensation detection means.

(3) The present invention also provides a walking rehabilitation supporting apparatus that supports rehabilitation for a patient having walking difficulty to acquire accurate walking behavior, including: a sensation detection unit for detecting sole pressure of the patient; a sensation presentation unit for imparting given stimulus to the patient; and a control unit for controlling behavior of the sensation presentation unit so as to impart stimulus corresponding to the sole pressure detected by the sensation detection unit, wherein the sensation detection unit is disposed so as to be capable of detecting the sole pressure on a paralyzed side, and the sensation presentation unit is fitted to a body surface portion of sensation superior to that of the foot sole.

(4) The sensation detection unit may be disposed so as to be capable of detecting the sole pressure on the paralyzed side and a non-paralyzed side of the patient, and the control unit may control the behavior of the sensation presentation unit according to a difference in sole pressure between the paralyzed side and the non-paralyzed side.

(5) The sensation detection unit may be disposed so as to be capable of detecting the sole pressure on the paralyzed side and the non-paralyzed side of the patient, and the control unit may control the behavior of the sensation presentation unit so as to switch between stimulus corresponding to the sole pressure on the paralyzed side and stimulus corresponding to the sole pressure on the non-paralyzed side and impart the stimulus to the body surface portion.

(6) It is preferable that the sensation detection unit includes a sole on which the foot sole is placed, and a pressure sensor for detecting the sole pressure of the patient for each of a plurality of regions in the sole, and the pressure sensor is disposed so as to be capable of detecting the sole pressure of each of the plurality of regions, the sensation presentation unit includes a stimulus imparting device for imparting stimulus to the skin so that the user receives touch-pressure sensation, vibratory sensation and/or movement sensation, the stimulus imparting device includes a plurality of pressing members provided correspondingly to the plurality of regions, and each of the pressing members imparts stimulus to the skin at intensity corresponding to the level of the sole pressure of the corresponding region.

Advantage of the Invention

According to the configuration in (1), biofeedback of dynamic action of the user to the environment is provided to a limb (body surface portion) of the user with somatic sensation, and thus validity of the dynamic action can be verified, and the user's adjustment of his/her action to the environment with awareness can be supported. At this time, somatic sensation information on a given body surface portion is fed back to the same body surface portion or a different body surface portion with somatic sensation information, and thus the user can more easily understand the fed-back information than the case of feedback with special sensation such as visual or auditory sensation. Also, there is no need for an apparatus such as a monitor or a processing such as image or sound conversion, thereby simplifying configurations and processings for information conversion, and making the apparatus compact and portable.

According to the configurations in (2) and (6), the somatic sensation information on the given body surface portion is fed back to the body surface portion using mechanical stimulus, and thus the somatic sensation can be fed back in more detail and easily understandable form with a simpler configuration than feedback using thermal stimulus, chemical stimulus, and electrical stimulus.

According to the configuration in (3), there is no need for a special mechanism or apparatus, and processings on the behavior can be easily performed, thereby simplifying and reducing the size of the entire apparatus to make the entire apparatus easily portable. Thus, walking rehabilitation training can be performed in any place.

Also, with basic learning about sensations, the patient can train by him/herself to acquire proper behavior of the limb on the paralyzed side on the basis of the somatic sensation information received by the body surface portion of sensation superior to that of the foot sole without attendance of a physical therapist. This sufficiently allows self-rehabilitation of the patient and does not limit a training time with attendance of the physical therapist, and thus the walking rehabilitation supporting apparatus is very useful for rehabilitation.

A hemiplegic patient wearing the walking rehabilitation supporting apparatus according to the present invention can receive sensation of the foot sole on the paralyzed side, on the body surface portion of sensation superior to that of the foot sole. Thus, the hemiplegic patient can easily acquire movement images for stable walking with improved inversion or eversion grounding specific to the hemiplegic patient, and can easily adjust his/her body posture or movement pattern for stable walking, and thus an advantage of mitigating his/her fear for falling at an early stage can be expected.

The tactile sensation of the foot sole on the paralyzed side is fed back to the body surface portion of sensation superior to that of the foot sole, thereby organization of perception and movement that are the most essential in cognitive therapeutic movement is significantly facilitated.

According to the configuration in (4), a left-right imbalance between the non-paralyzed side and the paralyzed side during standing specific to the hemiplegic patient can be improved to allow rehabilitation for the patient to stand upright.

According to the configuration in (5), the stimulus corresponding to the sole pressure on the non-paralyzed side is first imparted to the body surface portion, and thus target proper presentation stimulus is imparted to the body surface portion, and the patient can generate target presentation stimulus (teacher data) by him/herself. Switching so as to impart the stimulus corresponding to the sole pressure on the paralyzed side to the body surface portion allows the above described rehabilitation based on the teacher data. Specifically, the patient can confirm presentation stimulus in a target proper grounding state (for example, heel grounding) using his/her foot on the non-paralyzed side, and can generate the presentation stimulus so as to be the teacher data in rehabilitation for the paralyzed side by him/herself, thereby further contributing to self-rehabilitation.

DESCRIPTION OF SYMBOLS 10 walking rehabilitation supporting apparatus (sensation detection presentation apparatus)
11 sensation detection unit (sensation detection means)
13 sensation presentation unit (sensation presentation means)
15 control unit
18 pressure sensor
22 stimulus imparting device
32 pressing member
60 pressure measuring unit (sensation detection means)
62 operation command unit (sensation presentation means)
A forearm (body surface portion)
H patient (user)
P1 hallux region
P2 thenar region
P3 hypothenar region
P4 middle outer side region
P5 heel region
S sole

BEST MODE FOR CARRYING OUT THE INVENTION

Now, an embodiment of the present invention will be described with reference to the drawings.

Figure 1:
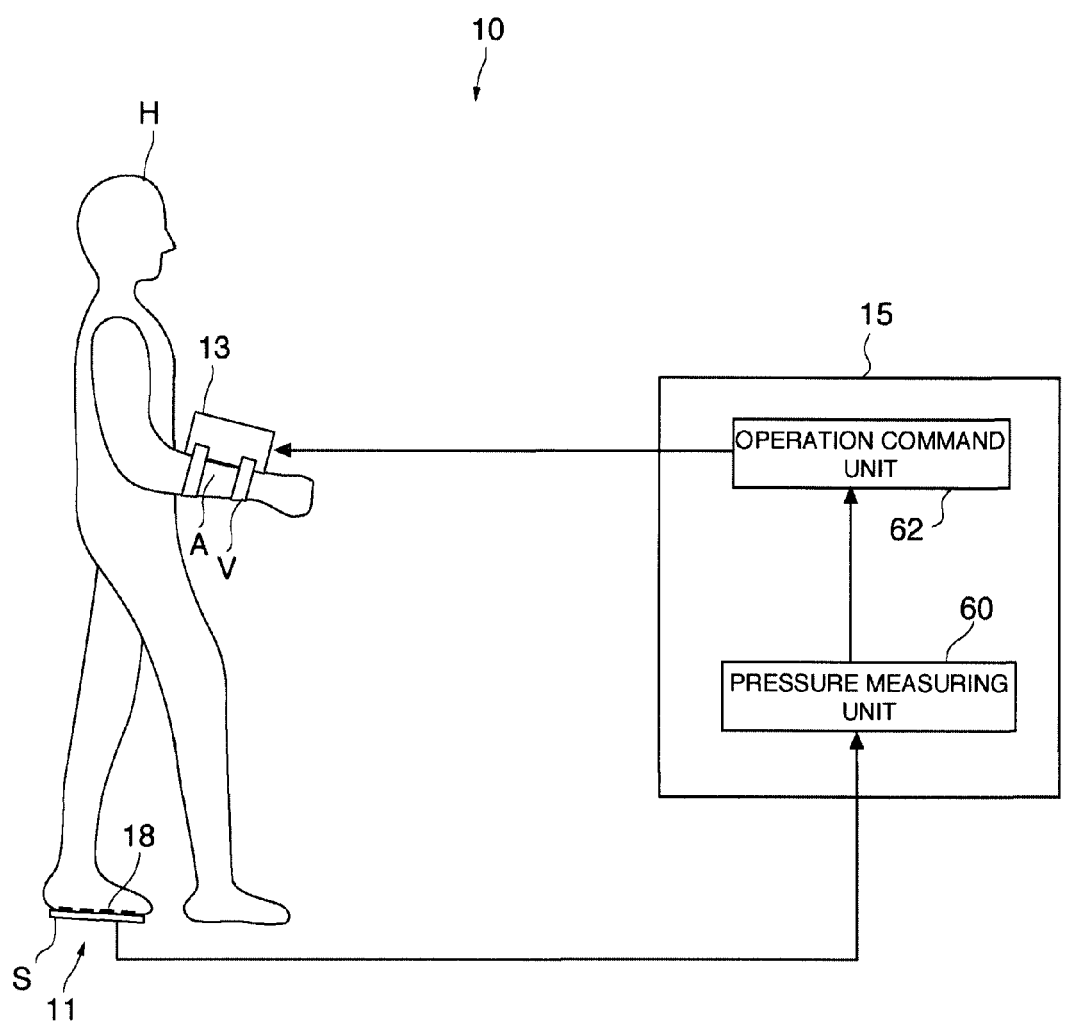
FIG. 1 is a schematic diagram of a walking rehabilitation supporting apparatus according to an embodiment of the present invention.

FIG. 1 is a schematic diagram of a walking rehabilitation apparatus according to the embodiment. In FIG. 1, a walking rehabilitation supporting apparatus 10 (sensation detection presentation apparatus) supports rehabilitation for a hemiplegic patient H (user) with a movement disorder on a right or left side to acquire accurate walking behavior. In the embodiment, the left side of the patient H is a paralyzed side, and the right side of the patient H is a non-paralyzed side.

The walking rehabilitation supporting apparatus 10 includes a sensation detection unit 11 for detecting sole pressure on the paralyzed side of the patient H, a sensation presentation unit 13 fitted to a forearm A on the non-paralyzed side of the patient H for imparting given stimulus to the forearm A, and a control unit 15 for controlling behavior of the sensation presentation unit 13 correspondingly to detection by the sensation detection unit 11.

The sensation detection unit 11 includes a sole S placed on an inside bottom of unshown footwear such as a shoe or a sandal and on which a foot sole is placed, and a plurality of pressure sensors 18 provided on a plurality of places on a surface of the sole S and disposed so as to be capable of detecting the sole pressure of the patient H.

Figure 2:
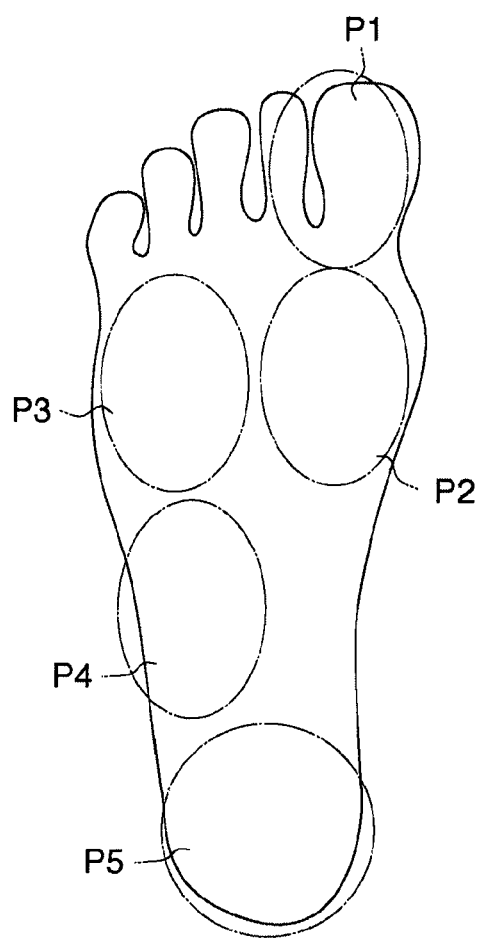
FIG. 2(A) shows a foot sole for illustrating regions for detection of sole pressure.
FIG. 2(B) is a schematic plan view of a sensation detection unit.
Figure 2:
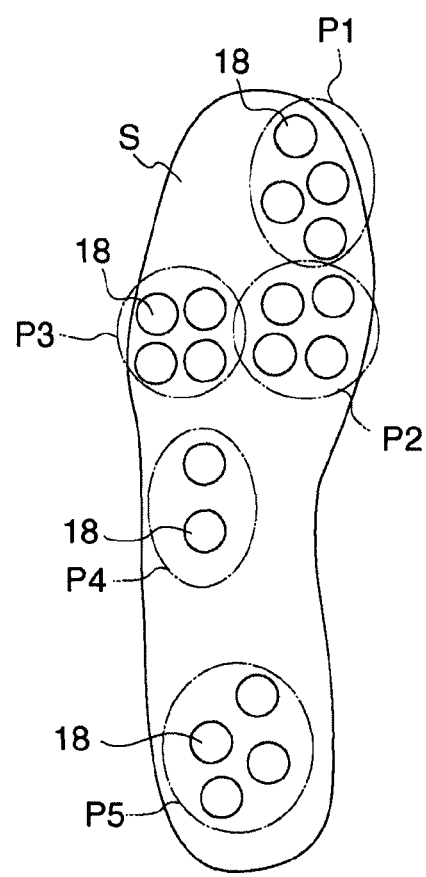

As the pressure sensors 18, known thin FSR (Force Sensing Resister) sensors are used, though not limited thereto. The pressure sensors 18 are provided on portions on the sole S substantially opposed to regions P1 to P5 in FIG. 2(A). Specifically, as shown in FIG. 2(B), the plurality of pressure sensors 18 are provided on the portions opposed to a hallux region P1, a thenar region P2, a hypothenar region P3, a middle outer side region P4, and a heel region P5 on the foot sole of the patient H. The pressure sensors 18 each can detect the sole pressure of the patient H, and as described later, the control unit 15 combines detection results of the pressure sensors 18 for each of the regions P1 to P5 to obtain sole pressure applied to each of the regions P1 to P5.

Figure 3:
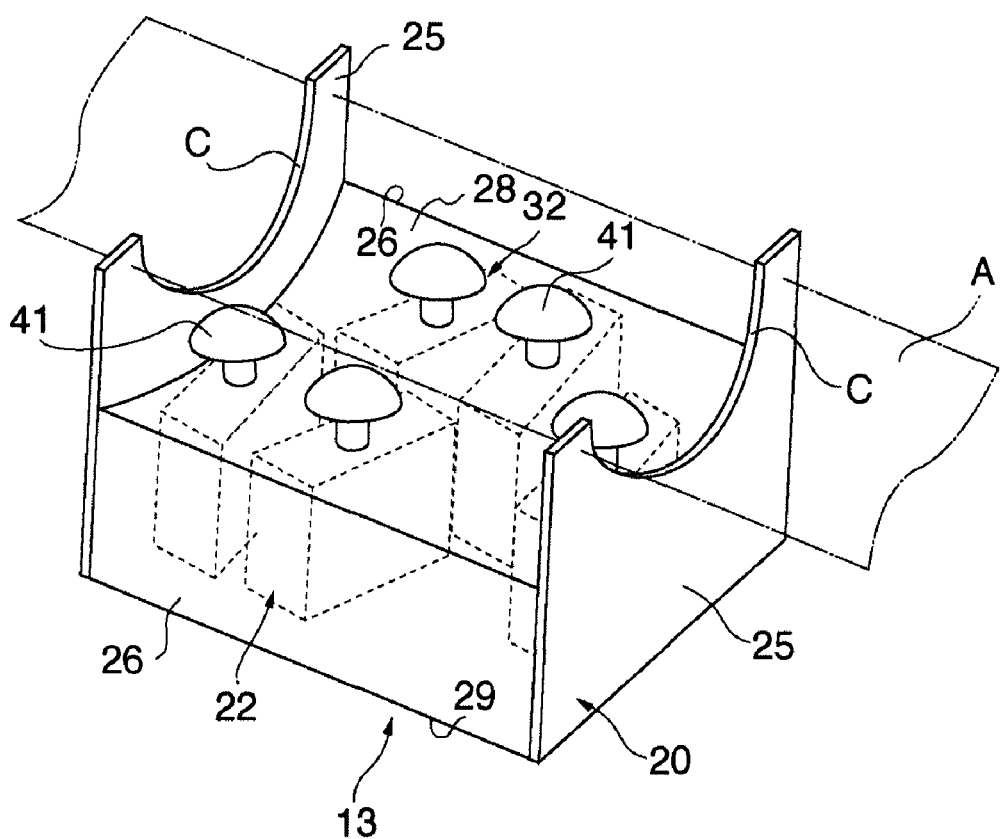
FIG. 3 is a schematic perspective view of the sensation detection unit.

As shown in FIG. 3, the sensation presentation unit 13 includes a cover 20 secured to the forearm A by a belt V (see FIG. 1), and a stimulus imparting device 22 that is placed in the cover 20 and imparts stimulus to skin of the forearm A so that the patient H receives touch-pressure sensation.

The cover 20 includes arch-shaped end walls 25 and 25 placed to stand on the forearm A at front and rear places of the forearm A, a side wall 26 placed on a lower lateral side of the end walls 25 and 25 in FIG. 3, a curved inner wall 28 placed between the end walls 25 and 25 and connecting to an upper end of the side wall 26 in FIG. 3, and an outer wall 29 connecting to a lower end of the side wall 26 in FIG. 3. A portion surrounded by the end walls 25, the side wall 26, the inner wall 28, and the outer wall 29 is an inner space housing the stimulus imparting device 22.

Each of the end walls 25 has a substantially arcuate notch C in an upper side in FIG. 3, and the notch C receives the forearm A.

The inner wall 28 has a curved shape substantially along an outer periphery of the forearm A received by the notch C.

Five stimulus imparting devices 22 are provided correspondingly to the regions P1 to P5 on the foot sole of the patient H as described later. The stimulus imparting devices 22 have the same structure, and each include, as shown in FIGS. 4 and 5, a box-shaped cover 30, a pressing member 32 protruding from an upper side of the cover 30 in FIG. 4, and an operation mechanism 34 (see FIG. 5) that is placed inside the cover 30 and operates the pressing member 32 in a vertical direction in FIG. 4.

Figure 4:
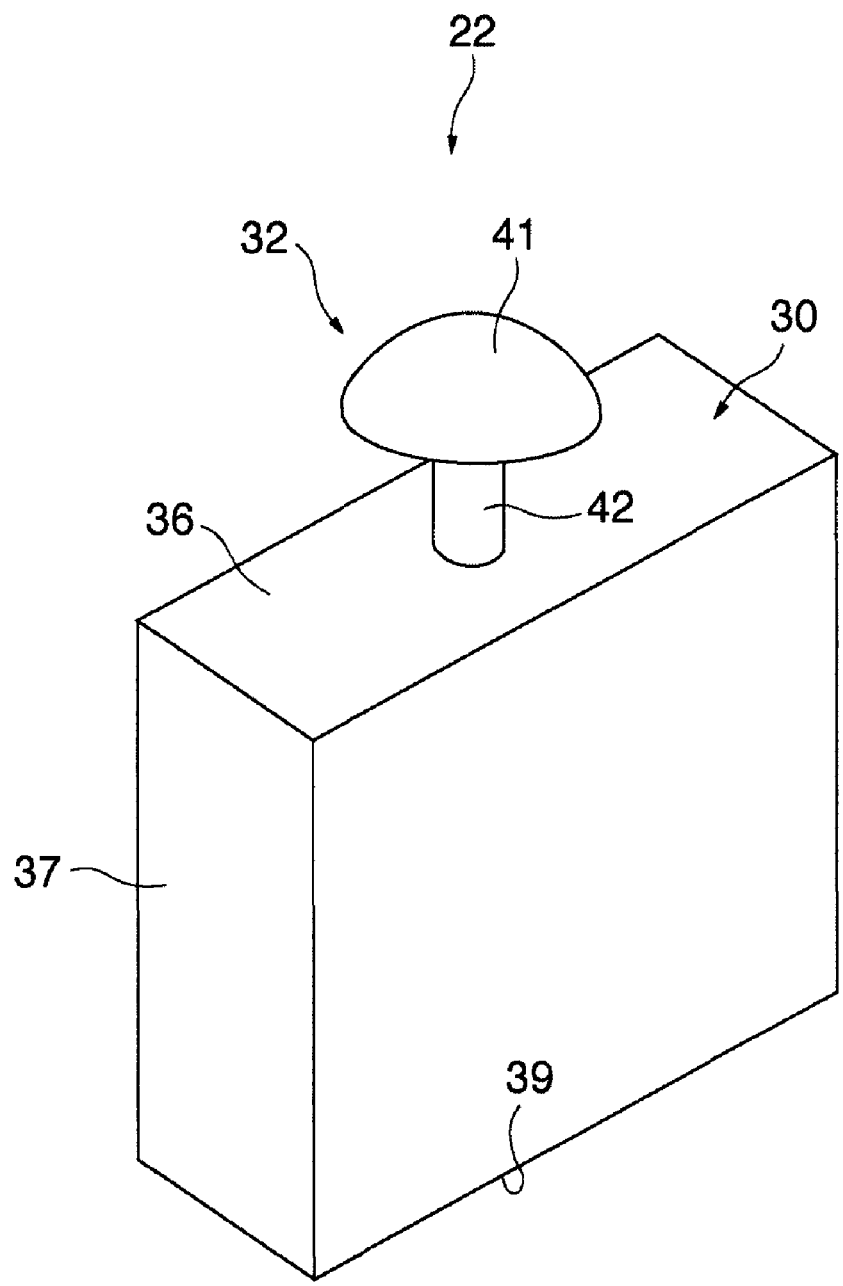
FIG. 4 is a schematic perspective view of a stimulus imparting device.

The cover 30 includes a top wall 36 located on an upper side in FIG. 4 and having a substantially square shape on plan view, a side wall 37 extending downward from a peripheral edge of the top wall 36 to a lower side in FIG. 4, and a bottom wall 39 connecting to a lower end of the side wall 37 in FIG. 4, though not limited thereto.

The pressing member 32 includes a pad 41 formed of an elastic body such as rubber into a cap shape so that a center thereof expands upward in FIG. 4, and a pin 42 secured to a lower end of the pad 41 in FIG. 4 and extending through the top wall 36 into the cover 30.

Figure 5:
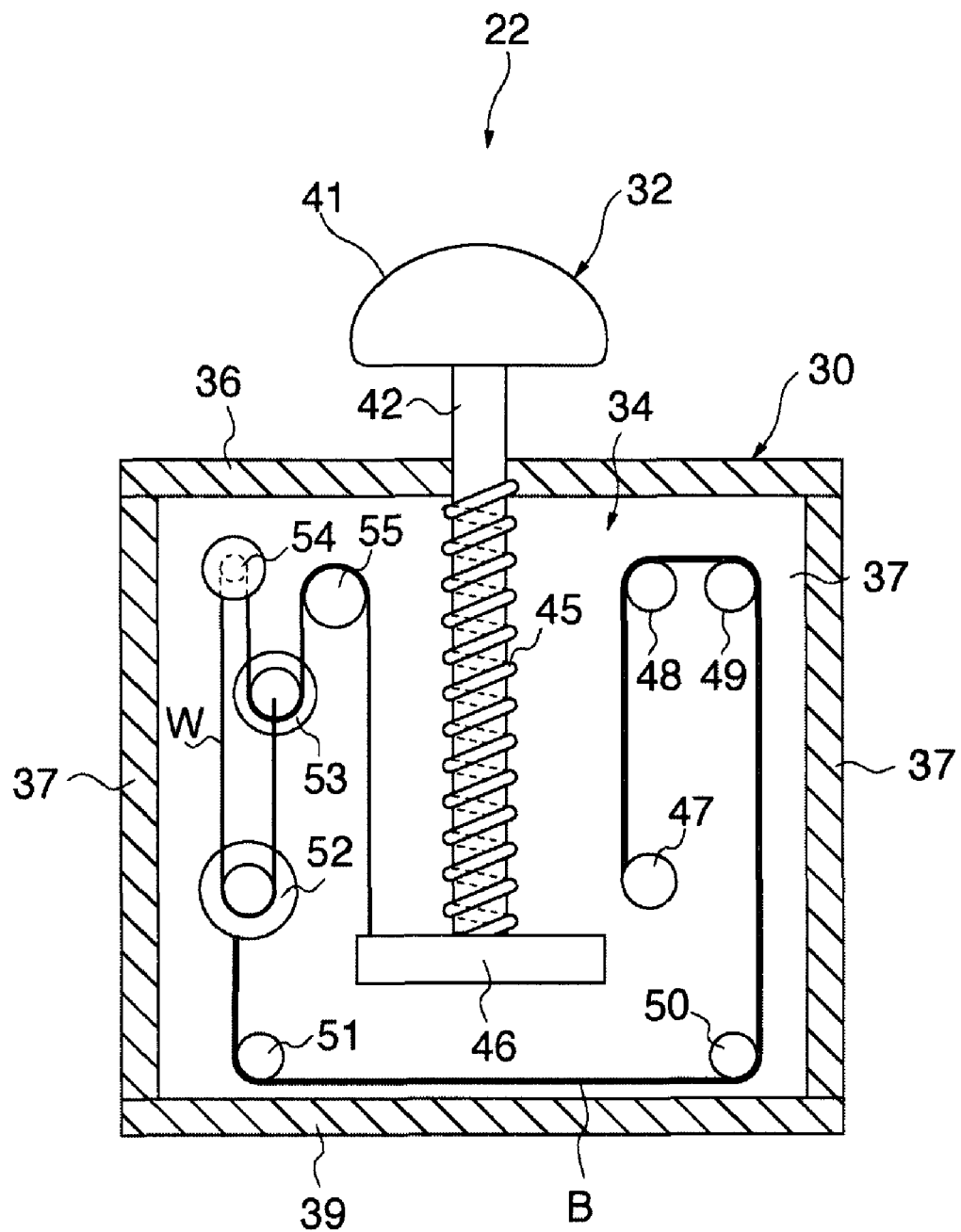
FIG. 5 is a schematic vertical sectional view of the stimulus imparting device.

The operation mechanism 34 includes a coil spring 45 wound around the pin 42, a plate 46 secured to a lower end of the pin 42 in FIG. 4, pulleys 47 to 51 rotatably secured to the side wall 37, a shape memory wire B having one end secured to the pulley 47 and wound around the other pulleys 48 to 51, a first running block 52 to which the other end of the shape memory wire B is secured, a second running block 53 located above the first running block 52 in FIG. 5, pulleys 54 and 55 rotatably secured to the side wall 37 at two places above the second running block 53 in FIG. 5, and a wire W wound around the first and second running blocks 52 and 53 and the pulleys 54 and 55.

The coil spring 45 has one end secured to the top wall 36 and the other end secured to the plate 46 so as to bias the pin 42 in a vertical direction in FIG. 5.

The shape memory wire B is made of a shape memory alloy such as a Ti—Ni alloy or a Ti—Ni—Cu alloy that can contract with heat when a current flows therethrough as disclosed in, for example, Japanese Patent Laid-Open No. 2005-193583 and Japanese Patent Laid-Open No. 57-141704. When the current stops flowing in the contracting state, the alloy extends to its original state. The shape memory wire B is electrically connected though not shown, and an amount of applied current changes on the basis of control by the control unit 15, which changes an amount of contraction of the wire B.

The wire W is made of a material that cannot be extended or contracted by an external force, one end of the wire is secured to the second running block 53, and the wire is extended therefrom and wound around the first running block 52, the pulley 54, the second running block 53, and the pulley 55 in order, and the other end is secured to the plate 46.

The operation mechanism 34 thus configured operates the pressing member 32 in the vertical direction as described below. First, when a current of an amount controlled by the control unit 15 flows through the shape memory wire B in an initial state in FIG. 5, the shape memory wire B contracts by its characteristic. Thus, the first running block 52 is drawn downward in FIG. 5, and thus the wire W moves with the second running block 53 moving downward, and the plate 46 is lifted upward in FIG. 5 against the biasing force of the coil spring 45. Thus, the pin 42 moves upward in FIG. 5 and the pad 41 protrudes. At this time, the amount of contraction of the shape memory wire B changes according to the amount of the current applied to the shape memory wire B, and thus an amount of upward movement of the pressing member 32 in FIG. 5 changes. Specifically, the control unit 15 controls an amount of protrusion of the pad 41. Then, when the supply of the current to the shape memory wire B is stopped, the shape memory wire B extends to its original length, and is operated in a manner reverse to the above by the biasing force of the coil spring 45, and the pad 41 and the pin 42 together with the plate 46 move downward in FIG. 5.

As shown in FIG. 3, the stimulus imparting devices 22 are arranged so that five pads 41 thereof are located in a positional relationship corresponding to the regions P1 to P5 including the pressure sensor 18 (see FIG. 2), and that the forearm A does not come into contact with the pads 41 in the initial state when the notch C receives the forearm A. Then, as described above, the control unit 15 controls the operation of the operation mechanism 34 (see FIG. 5) of each stimulus imparting device 22, and the given pad 41 protrudes to press the forearm A. Thus, stimulus is imparted to the skin of the forearm A on the non-paralyzed side of the patient H, and the patient H receives touch-pressure sensation. The pads 41 are arranged correspondingly to the regions P1 to P5 (see FIG. 2), but may be arranged correspondingly to the pressure sensors 18. The stimulus imparting devices 22 can be arranged in various ways as long as the forearm A can receive stimulus in a manner as if a footprint on the paralyzed side were transferred to the forearm A on the non-paralyzed side. For example, the stimulus imparting devices 22 may be arranged so that the arrangement of the regions P1 to P5 is scaled up or down in lateral and vertical directions. A scale-up or scale-down ratio at this time needs not be always an equal ratio.

The control unit 15 is constituted by a given computer and connected between the sensation detection unit 11 and the sensation presentation unit 13 via wired or wireless connection or via a given line so that data is transmitted and received therebetween. The control unit 15 needs only perform an easy processing as described above, and may be portable and may be fittable to a waist or the like of the patient H, though not limited thereto.

As shown in FIG. 1, the control unit 15 includes a pressure measuring unit 60 for combining the detection results of the pressure sensors 18 for each of the regions P1 to P5 to obtain the sole pressure of each of the regions P1 to P5, and an operation command unit 62 for issuing an operation command to the sensation presentation unit 13 so as to operate the pressing member 32 corresponding to each of the regions P1 to P5 according to the sole pressure of each of the regions P1 to P5 obtained by the pressure measuring unit 60. Thus, the sensation detection unit 11 and the pressure measuring unit 60 constitute sensation detection means for detecting the sole pressure (somatic sensation information) of the foot sole on the paralyzed side (first body surface portion). The sensation presentation unit 13 and the operation command unit 62 constitute sensation presentation means for presenting touch-pressure sensation information (somatic sensation information) corresponding to the sole pressure detected by the sensation detection means to the forearm A on the non-paralyzed side as a second body surface portion.

The operation command unit 62 is set so as to classify the sole pressure into given levels in stages (about 3 to 5 stages in the embodiment) and change the amount of movement of the pressing member 32 for each level in stages. The present invention is not limited thereto, but the pressing member 32 may be moved without stages correspondingly to the sole pressure. The operation command unit 62 is set so that the amount of movement of the pressing member 32 increases with increasing sole pressure, but may be set so that the amount of movement of the pressing member 32 decreases with increasing sole pressure.

Next, a procedure of rehabilitation using the walking rehabilitation supporting apparatus 10 will be described.

First, the patient H sitting on a chair or the like visually checks a grounding state of the foot on the paralyzed side moved by an attendant. At this time, the sensation presentation unit 13 applies a pressing force corresponding to the grounding state to the forearm A on the non-paralyzed side, and the patient H memorizes the pressing force by cutaneous sensation (touch-pressure sensation) and learns matching the pressing force sensed at this time and the visually checked grounding state. For example, when the heel only on the paralyzed side is placed on the ground, the patient H visually checks the grounding state of the heel only and confirms the state. At this time, a load is applied to the heel in a concentrated manner, and thus high sole pressure is detected on the heel by the sensation detection unit 11. In the sensation presentation unit 13, the pressing member 32 in the position corresponding of the heel region P5 presses the forearm A on the non-paralyzed side with intensity corresponding to the sole pressure, and the patient H memorizes the pressed area and the intensity of the stimulus and learns that when the pressed area only receives touch-pressure sensation, the heel only on the paralyzed side is actually placed on the ground. The grounding state learned here includes a grounding pattern, a difference in intensity of the sole pressure, and a moving direction of the sole pressure.

Next, the patient H sitting on the chair or the like does not visually check the grounding state of the foot on the paralyzed side moved by the attendant, but recalls the cutaneous sensation previously learned and answers the grounding state of the foot on the paralyzed side from the position and intensity of the touch-pressure sensation presented to the forearm A by the sensation presentation unit 13, using pictures or the like showing the grounding state. This confirms a learning effect of matching the position and intensity of the touch-pressure sensation presented to the forearm A by the sensation presentation unit 13 and the grounding state of the foot on the paralyzed side.

After the above described previous learning, actual rehabilitation is performed. Specifically, the patient H adjusts movement of the foot and/or the limb other than the foot on the paralyzed side on the basis of information on the touch-pressure sensation presented to the forearm A on the non-paralyzed side of the patient H so as to obtain a target grounding state of the foot during walking or the like. For example, in a state where the entire foot on the paralyzed side is substantially placed on the ground, the sole pressure of the regions P1 to P5 is low and substantially uniform. In this case, all the pressing members 32 substantially uniformly apply weak pressing forces to the forearm A on the non-paralyzed side. The patient H has memorized the matching between such touch-pressure sensation and the actual grounding state from the previous learning. Thus, when the state where the entire foot on the paralyzed side is substantially placed on the ground is set as a target, and there is a dispersion in touch-pressure sensation presented to the forearm A, the patient H realizes that the foot on the paralyzed side is not in the target grounding state, and adjusts the movement of the foot and/or the limb other than the foot on the paralyzed side so as to eliminate the dispersion in touch-pressure sensation presented to the forearm A. Specifically, the patient H can voluntarily acquire proper movement for obtaining the target grounding state using the sensation presented to the forearm A.

The patient H may perform the above described procedure while sitting on the chair or the like or standing. The same applies to the reverse setting of the operation command unit 62, that is, the case where the amount of movement of the pressing member 32 decreases with increasing sole pressure.

Thus, according to the embodiment, self-rehabilitation can be supported that is performed by the patient H him/herself noting the sensation or movement state of his/her body.

As a variant of the embodiment, specifications of the control unit 15 may be changed for rehabilitation from other viewpoints. Specifically, in this case, the sensation detection unit 11 is also fitted to the foot on the non-paralyzed side. The pressure measuring unit 60 at this time is set so as to be able to calculate a difference in sole pressure between the non-paralyzed side and the paralyzed side for each of the regions P1 to P5. The operation command unit 62 is set so as to change the amount of movement of the pressing member 32 in stages correspondingly to the difference in sole pressure between the non-paralyzed side and the paralyzed side. Specifically, the operation command unit 62 here is set so as to minimize the amount of movement of the pressing member 32 in a target grounding state with little difference in sole pressure between left and right sides and increase the amount of movement of the pressing member 32 according to the difference in sole pressure between the left and right sides when weight is applied to the non-paralyzed side. Thus, the patient H standing can perceive a state of the center of gravity offset to the non-paralyzed side specific to the hemiplegic patient H from the touch-pressure sensation on the forearm A on the non-paralyzed side by the sensation presentation unit 13. Also, the patient H can adjust the movement of the limb including the paralyzed side so as to substantially eliminate the touch-pressure sensation presented to the forearm A and thus can gradually acquire movement for correcting a left-right imbalance during standing. Specifically, according to the variant, the left-right imbalance between the non-paralyzed side and the paralyzed side during standing specific to the hemiplegic patient H can be improved to allow rehabilitation for the patient to stand upright. Contrary to the above, the operation command unit 62 may be set so as to maximize the amount of movement of the pressing member 32 in the target grounding state with little difference in sole pressure between the left and right sides and decrease the amount of movement of the pressing member 32 according to the difference in sole pressure between the left and right sides when weight is applied to the non-paralyzed side.

Further, another variant described below may be used. Specifically, the sensation detection units 11 are fitted to both feet on the paralyzed side and the non-paralyzed side, and the pressure measuring unit 60 can measure the sole pressure of each of the regions P1 to P5 on each of the non-paralyzed side and the paralyzed side. The operation command unit 62 here can switch between a paralyzed side stimulus presentation mode (normal mode) in which the pressing member 32 is moved according to the sole pressure on the paralyzed side and a non-paralyzed side stimulus presentation mode in which the pressing member 32 is moved according to the sole pressure on the non-paralyzed side with a switch or the like. In this case, first, the patient H selects the non-paralyzed side stimulus presentation mode, the sensation presentation unit 13 imparts stimulus corresponding to the sole pressure on the non-paralyzed side to the forearm A on the non-paralyzed side and thus imparts target proper presentation stimulus to the body surface portion of the patient H, and thus the patient H generates target presentation stimulus (teacher data) by him/herself. Then, the patient H switches to the normal mode, and stimulus corresponding to the sole pressure on the paralyzed side is imparted to the forearm A of the patient H, and thus the walking rehabilitation described in the embodiment is performed on the basis of the teacher data. According to the variant, the presentation stimulus when the target proper grounding state (for example, heel grounding) is reproduced can be confirmed using the foot on the non-paralyzed side of the patient, and the patient H can acquire the teacher data by him/herself, thereby further facilitating self-rehabilitation.

In the embodiment and the variants, the sensation detection unit 11 detects the touch-pressure sensation of the foot sole to provide biofeedback, but the present invention is not limited thereto. The sensation detection unit 11 may detect somatic sensation information on other body surface portions such as front of head, back of head, face, forehead, lips, fingertip, finger or hand other than fingertip, lateral surface of upper arm, shoulder, upper back, lower back, abdomen, leg, or hip to provide biofeedback. The detected somatic sensation information includes the touch-pressure sensation described above and other cutaneous sensations such as vibratory sensation, movement sensation, temperature sensation, and pain sensation, and deep sensations such as position sensation.

The sensation presentation unit 13 may be fitted not only to the forearm A but also to other body surface portions on the non-paralyzed side, such as front of head, back of head, face, forehead, lips, fingertip, finger or hand other than fingertip, lateral surface of upper arm, shoulder, upper back, lower back, abdomen, leg, or hip, or to body surface portions with a low level of paralysis.

The sensation detection unit 11 may detect somatic sensation information on a plurality of given places, and the sensation presentation unit 13 may present the somatic sensation information to the plurality of given places on the basis of the detection results. The sensation detection unit 11 may detect somatic sensation information on the plurality of given places and collect the detection results, and the sensation presentation unit 13 may present the somatic sensation information to one given place. Contrary to this, the sensation detection unit 11 may detect somatic sensation information on one given place, and the sensation presentation unit 13 may present somatic sensation information to a plurality of given places on the basis of the detection result.

Further, the sensation presentation unit 13 may be able to impart different mechanical stimulus, thermal stimulus, chemical stimulus and/or electrical stimulus to the body surface portion on the basis of the somatic sensation information detected by the sensation detection unit 11.

The sensation presentation unit 13 that imparts the different mechanical stimulus may have an exemplary configuration modified from the configuration of the embodiment, in which ON/OFF of application of the current to the shape memory wire B in FIG. 5 is repeated in a short time to vibrate the pressing member 32 in the vertical direction in FIG. 5 at a frequency corresponding to the somatic sensation information detected by the sensation detection unit 11 to present vibratory sensation to the skin. Also, the pressing member 32 may be movable along the inner wall 28 in FIG. 3 and move a distance corresponding to the somatic sensation information detected by the sensation detection unit 11 to present movement sensation to the skin. Alternatively, pressure stimulus or vibration stimulus may be presented using a solenoid, air pressure, a piezoelectric element, or the like. Specifically, any stimulus imparting device 22 may be used as long as it imparts mechanical stimulus to the skin of the patient H so that the patient H receives touch-pressure sensation, vibratory sensation and/or movement sensation.

The sensation presentation unit 13 that imparts the thermal stimulus may have an exemplary configuration in which the pad 41 that comes into contact with the skin can be heated or cooled, and the pad 41 is brought into contact with the skin at a temperature corresponding to the somatic sensation information detected by the sensation detection unit 11 to present warm sensation or cold sensation to the skin. However, the warm and cold sensations change according to a stimulus area, a temperature change speed, an adaptation state, or the like, the temperature cannot be controlled at high speed, and the size of the entire apparatus is increased, and thus the above described configuration for imparting the mechanical stimulus is preferably used.

Further, the sensation presentation unit 13 that imparts the chemical stimulus may have an exemplary configuration in which a liquid that presents cool sensation or pain sensation when coming into contact with the skin can be injected to the skin, and an amount of injection thereof corresponds to the somatic sensation information detected by the sensation detection unit 11.

The sensation presentation unit 13 that imparts the electrical stimulus to the body surface portion may have an exemplary configuration in which electrodes are placed in a plurality of areas near the skin, and a current of an amount corresponding to the somatic sensation information detected by the sensation detection unit 11 is applied to the electrodes to present electrical pain sensation or tactile sensation to the skin. However, when the electrical stimulus is used, a stimulus intensity range between the intensity for no stimulus and the intensity for pain stimulus is extremely narrow, and also significant threshold changes occur during stimulus imparting due to sweating or the like, and thus the above described configuration for imparting the mechanical stimulus is preferably used.

Further, in the embodiment and the variants, the case where the sensation detection presentation apparatus of the present invention is applied to the walking rehabilitation supporting apparatus 10 is shown and described, but the present invention is not limited thereto, and may be applied to other apparatuses that need to present somatic sensation information on a first body surface portion to a second body surface portion as a different portion.

For example, the present invention may be applied to a tactile sensation presentation apparatus in which a sensation presentation unit 13 presents cutaneous sensation information on fingers of a left or right hand detected by the sensation detection unit 11 to fingers of the other hand. Thus, information required for operating an object such as information on grasping feeling or a force level by the paralyzed hand can be obtained, and on the basis of the information, the way of movement of the paralyzed hand can be adjusted. Specifically, the patient can perform rehabilitation while imaging in detail the force level of the fingertips of the paralyzed hand, thereby providing a rehabilitation effect of increasing handiness.

The present invention may be applied to a rehabilitation shoe device for detecting sole pressure on a paralyzed side, and presenting pressure stimulus to a foot sole on the paralyzed side to amplify stimulus to the foot sole on the paralyzed side. This device imparts the pressure stimulus obtained by amplifying the actual sole pressure as the foot sole on the paralyzed side is placed on the ground, thereby allowing rehabilitation for sensation paralysis.

Further, the present invention may be applied to an apparatus for detecting somatic sensation information on sole pressure of a prosthetic foot or pressure stimulus to fingers of a prosthetic hand to present stimulus based on the information to areas other than the prosthetic foot or hand.

The configurations of the components of the apparatus according to the present invention are not limited to the shown exemplary configurations, but various changes may be made as long as the configurations have substantially the same operations.

The invention claimed is:

1. A walking rehabilitation supporting apparatus that supports rehabilitation for a patient having walking difficulty to acquire accurate walking behavior, comprising:
   a sensation detection unit configured for detecting sole pressure of said patient;
   a sensation presentation unit configured for imparting stimulus to said patient;
   a control unit for controlling behavior of said sensation presentation unit so as to impart stimulus corresponding to the sole pressure detected by said sensation detection unit,
   wherein said sensation detection unit is configured for detecting the sole pressure on a paralyzed side and a non-paralyzed side of said patient, and
   said sensation presentation unit is configured to fit a body surface portion of said patient and provide sensation superior to that of said foot sole of said paralyzed side, and
   said control unit is further configured to control the behavior of said sensation presentation unit according to a difference in sole pressure between said paralyzed side and said non-paralyzed side.

2. A walking rehabilitation supporting apparatus that supports rehabilitation for a patient having walking difficulty to acquire accurate walking behavior, comprising:
   a sensation detection unit configured for detecting sole pressure of said patient;
   a sensation presentation unit configured for imparting stimulus to said patient; and
   a control unit for controlling behavior of said sensation presentation unit so as to impart stimulus corresponding to the sole pressure detected by said sensation detection unit;
   wherein said sensation detection unit is configured for detecting the sole pressure on a paralyzed side and a non-paralyzed side of said patient, said sensation presentation unit is configured to fit a body surface portion of said patient and provide sensation superior to that of said foot sole of said paralyzed side, and
   said control unit is further configured to control the behavior of said sensation presentation unit so as to switch between stimulus corresponding to the sole pressure on said paralyzed side and stimulus corresponding to the sole pressure on said non-paralyzed side and to impart the stimulus to said body surface portion.

3. The walking rehabilitation supporting apparatus according to claim 1 or 2, wherein said sensation detection unit includes two soles configured for placement on said paralyzed side and said non-paralyzed side, respectively, and pressure sensors for detecting sole pressure of the patient for each of a plurality of regions in the respective soles, and said pressure sensors are disposed so as to be capable of detecting the sole pressures of said plurality of regions,
   said sensation presentation unit includes a stimulus imparting device configured for imparting the stimulus to the skin so that said patient receives touch-pressure sensation, vibratory sensation and/or movement sensation, wherein said stimulus imparting device includes a plurality of pressing members provided correspondingly to said plurality of regions, and each of said pressing members is configured to impart stimulus to the skin at an intensity corresponding to the level of the sole pressure of the corresponding region.

* * * * *